US012246107B2

(12) United States Patent
Nicolas et al.

(10) Patent No.: US 12,246,107 B2
(45) Date of Patent: Mar. 11, 2025

(54) MULTI-LAYER BAG WITH LOSS OF INTEGRITY MEANS OF DETECTION

(71) Applicant: Becton Dickinson France, Le Pont de Claix (FR)

(72) Inventors: Maxime Nicolas, Grenoble (FR); Julien Guillemot, Thorigne-Fouillard (FR)

(73) Assignee: Becton Dickinson France, Le Pont de Claix (FR)

( * ) Notice: Subject to any disclaimer, the term of this patent is extended or adjusted under 35 U.S.C. 154(b) by 896 days.

(21) Appl. No.: 17/289,978

(22) PCT Filed: Oct. 28, 2019

(86) PCT No.: PCT/EP2019/079367
§ 371 (c)(1),
(2) Date: Apr. 29, 2021

(87) PCT Pub. No.: WO2020/089156
PCT Pub. Date: May 7, 2020

(65) Prior Publication Data
US 2021/0402032 A1    Dec. 30, 2021

(30) Foreign Application Priority Data

Oct. 31, 2018 (EP) ..................................... 18306426

(51) Int. Cl.
*A61L 2/28* (2006.01)
*A61B 50/30* (2016.01)
(Continued)

(52) U.S. Cl.
CPC ................ *A61L 2/28* (2013.01); *A61B 50/30* (2016.02); *A61L 2/20* (2013.01); *B32B 1/00* (2013.01);
(Continued)

(58) Field of Classification Search
CPC .......... A61L 2/28; A61L 2/20; A61L 2202/12; A61L 2202/181; A61L 2202/24;
(Continued)

(56) References Cited

U.S. PATENT DOCUMENTS 4,097,236 A     6/1978  Daly et al.
5,222,600 A *   6/1993  Stoddard ................ B65D 33/24
                                                             206/439

(Continued)

FOREIGN PATENT DOCUMENTS

CA      2038298 A1      10/1991
CN    101918045 A       12/2010
(Continued)

OTHER PUBLICATIONS

English translation of FR2521906 (Year: 1983).*

*Primary Examiner* — Regina M Yoo
(74) *Attorney, Agent, or Firm* — The Webb Law Firm

(57) ABSTRACT

A multi-layer bag comprising a porous portion configured to allow a sterilizing gas to penetrate into the bag and a gas-impervious portion, characterized in that the gas-impervious portion comprises an outer layer, an inner layer and an intermediate layer integrally formed together so that the intermediate layer is sealingly enclosed between the outer layer and the inner layer so as to be physically isolated from inner and outer environment of the bag, and the intermediate layer comprises a matrix and at least one pigment distributed within the matrix, the pigment being configured to change at least one optical property in reaction to an environment change resulting from a damage of the outer and/or inner layer.

20 Claims, 3 Drawing Sheets

(51) Int. Cl.
  *A61L 2/20* (2006.01)
  *B32B 1/00* (2006.01)
  *B32B 27/08* (2006.01)
  *B32B 27/20* (2006.01)
  *B32B 27/30* (2006.01)
  *B32B 27/32* (2006.01)
  *B32B 27/36* (2006.01)
  *B65B 5/04* (2006.01)
  *B65B 55/02* (2006.01)
  *B65D 33/00* (2006.01)
  *B65D 65/40* (2006.01)
  *G01N 31/22* (2006.01)

(52) U.S. Cl.
  CPC .............. *B32B 27/08* (2013.01); *B32B 27/20* (2013.01); *B32B 27/306* (2013.01); *B32B 27/327* (2013.01); *B32B 27/36* (2013.01); *B65B 5/045* (2013.01); *B65B 55/02* (2013.01); *B65D 33/004* (2013.01); *B65D 65/40* (2013.01); *G01N 31/226* (2013.01); *A61B 2050/316* (2016.02); *A61L 2202/12* (2013.01); *A61L 2202/181* (2013.01); *A61L 2202/24* (2013.01); *B32B 2250/03* (2013.01); *B32B 2250/24* (2013.01); *B32B 2270/00* (2013.01); *B32B 2307/4026* (2013.01); *B32B 2307/518* (2013.01); *B32B 2307/7242* (2013.01); *B32B 2439/46* (2013.01)

(58) Field of Classification Search
  CPC ....... A61L 2202/18; A61L 2/26; A61B 50/30; A61B 2050/316; B32B 1/00; B32B 27/08; B32B 27/20; B32B 27/306; B32B 27/327; B32B 27/36; B32B 2250/03; B32B 2250/24; B32B 2270/00; B32B 2307/4026; B32B 2307/518; B32B 2307/7242; B32B 2439/46; B65B 5/045; B65B 55/02; B65D 33/004; B65D 65/40; G01N 31/226

See application file for complete search history.

(56) References Cited

U.S. PATENT DOCUMENTS

| | | | |
|---|---|---|---|
| 8,679,846 B2 | 3/2014 | Ricard et al. | |
| 9,005,978 B2 | 4/2015 | Bottcher et al. | |
| 9,139,348 B2 | 9/2015 | Voute | |
| 2005/0079093 A1* | 4/2005 | Cannady | B65D 75/08 422/26 |
| 2006/0104856 A1* | 5/2006 | Farrell | B09B 3/0075 422/1 |
| 2009/0123332 A1 | 5/2009 | Whitehead et al. | |
| 2011/0308984 A1 | 12/2011 | Hennek | |
| 2012/0057810 A1 | 3/2012 | De Klerk et al. | |
| 2013/0095336 A1 | 4/2013 | Hermel-Davidock | |
| 2013/0168279 A1 | 7/2013 | Sandford | |
| 2013/0340394 A1* | 12/2013 | Cannady | A61L 2/26 229/87.01 |
| 2015/0306259 A1 | 10/2015 | Deutschle et al. | |
| 2016/0185498 A1* | 6/2016 | Henderson | B32B 37/12 156/60 |
| 2016/0330971 A1 | 11/2016 | Joseph | |
| 2016/0361232 A1 | 12/2016 | Chou et al. | |

FOREIGN PATENT DOCUMENTS

| | | | | |
|---|---|---|---|---|
| FR | 2521906 A1 | 8/1983 | | |
| FR | 2965556 A1 | 4/2012 | | |
| JP | 2002071570 A | 3/2002 | | |
| JP | 2006044776 A | 2/2006 | | |
| JP | 5336044 B2 | 11/2013 | | |
| JP | 2016073377 A | 5/2016 | | |
| JP | 2018518268 A | 7/2018 | | |
| WO | 9524933 A1 | 9/1995 | | |
| WO | 9836903 A1 | 8/1998 | | |
| WO | 2005056404 A1 | 6/2005 | | |
| WO | WO-2017109944 A1 * | 6/2017 | | A61F 7/03 |

* cited by examiner

MULTI-LAYER BAG WITH LOSS OF INTEGRITY MEANS OF DETECTION

CROSS-REFERENCE TO RELATED APPLICATIONS

This application is the United States national phase of International Application No. PCT/EP2019/079367 filed Oct. 28, 2019, and claims priority to European Patent Application No. 18306426.0 filed Oct. 31, 2018, the disclosures of which are hereby incorporated by reference in their entirety.

FIELD OF THE INVENTION

The invention relates to a multi-layer bag, more particularly to a multi-layer bag on which loss of integrity may be detected; and to a process for manufacturing such a multi-layer bag. The invention further relates to a process for detecting a loss of integrity of such a multi-layer bag.

BACKGROUND OF THE INVENTION

Often, devices such as medical devices or non-medical devices need to be transported from one site to another, when they are manufactured in one site and filled in another site, or, less frequently, when they are manufactured and filled in the same site and must be delivered, once filled, to another site.

Accordingly, bags may be used for packaging devices in a manufacturing plant in view of their shipment and storage at an end-user location. Devices may be medical devices such as syringes or tubs comprising syringes. The medical devices particularly useful for medical applications are packaged into bags to preserve their sterility (sterilization bags). These sterilization bags are intended to provide a barrier to prevent contaminants, including microorganisms, from entering inside the bag.

Accordingly, although the medical devices are produced in a clean room, a sterilization step is implemented after their packaging to destroy any contamination. Ethylene oxide (EtO) sterilization is a common method used to sterilize the bag.

To that end, the sterilization bags comprise a portion which is porous to gases and particularly to sterilization gases (e.g. ethylene oxide) and which is configured to allow said sterilizing gases to penetrate into the bag to be in contact with the medical devices.

The integrity of the sterilization bag has to be maintained until opening for final use of the medical device. Otherwise, there exists a risk that a contamination of the medical devices occurs, with possibly hazardous consequences for the patient.

The sterilization bags comprising the medical devices are packaged in boxes intended to protect the medical devices and sterilization bags from mechanical constraints that may damage them. However, it cannot be excluded that a breach be made in a sterilization bag, e.g. in case it is in contact with a sharp object.

A loss of integrity of the sterilization bag may not be easily visible, e.g. in the case of a small breach formed in a wall of the bag. Thus, even if the sterilization bag is apparently undamaged, the medical devices may have been contaminated through the breach.

In order to anticipate such a contamination of the medical devices, a decontamination may be carried out at the point of use. However, such a decontamination, which is applied to all the medical devices contained in a same box, is expensive and time-consuming.

Thus, it would be desirable to carry out such a decontamination only for the medical devices of which the sterilization bag has been damaged.

There exist indicators of a loss of integrity of a whole packaging that may be placed in a bag and that are configured to change color due to a chemical reaction when the atmosphere inside the bag changes.

However, such indicators cannot be used with the above-described sterilization bags. Indeed, due to the porous portion, the atmosphere inside and outside the bag is the same. Thus, a breach made in a wall of the bag would not change the atmosphere inside the bag and would thus not affect the color of the indicator.

SUMMARY OF THE INVENTION

A goal of the invention is to provide a multi-layer bag for medical devices, said multi-layer bag comprising a reliable way of indicating that the multi-layer bag has lost its integrity.

According to the invention, when the packaging has "lost its integrity", it is meant that the packaging has been damaged, perforated or torn up.

An embodiment provides a multi-layer bag comprising a porous portion configured to allow a sterilizing gas to penetrate into the bag and a gas-impervious portion, characterized in that:

the gas-impervious portion comprises an outer layer, an inner layer and an intermediate layer integrally formed together so that the intermediate layer is sealingly enclosed between the outer layer and the inner layer, and the intermediate layer comprises a matrix and a pigment distributed within the matrix, the pigment being configured to change at least one optical property in reaction to an environment change resulting from a damage of the outer and/or inner layer.

By "gas-impervious" is meant a portion with a low permeability to gases. The permeability of the gas-impervious portion may depend on the desired shelf life of the packaging, of the considered gas(es) and of the thickness of the porous portion. To that end, the inner and outer layers of the gas-impervious portion are non-porous, each of said layers having a low permeability to the considered gas(es).

By "environment change" is meant a change in the atmosphere to which the intermediate layer (and thus the pigment) is exposed. In a normal condition of the bag, the intermediate layer is physically isolated from the atmosphere outside and inside the bag (called "ambient atmosphere") by the outer and inner layers. The pigment thus has a first optical property (e.g. color) that depends on the condition of the pigment once placed between the outer and inner layers and isolated from the ambient atmosphere. When a breach is made in the gas-impervious portion of the bag, the intermediate layer is exposed to the ambient atmosphere, which triggers a change in the above-mentioned optical property (e.g. color) of the pigment.

The pigment may be configured to change color in at least one of the following situations:

(i) the intermediate layer is in contact with water, moist, or $H_2O_2$ in a liquid state;

(ii) the intermediate layer is in contact with a determined gas such as $O_2$, $CO_2$, $N_2$, Ar, $H_2$, NOX, $H_2O_2$, EtO or mixture thereof;

(iii) the intermediate layer is exposed to a pH change;

(iv) the intermediate layer is exposed to a change of radiation;

(v) a mechanical pressure is exerted onto the intermediate layer.

In some embodiments, the intermediate layer comprises at least two different pigments distributed within the matrix.

At least two of said pigments may have different optical properties in reaction to an environment change resulting from a damage of the outer and/or inner layer.

In some embodiments, at least two of said different pigments may be configured to change color in different situations among situations (i) to (v).

In some embodiments, at least two of said pigments are configured to change color in reaction to different levels of a same situation among situations (i) to (v).

At least one of the outer layer and the inner layer may comprise a polymer selected from the group consisting of: polyethylene, in particular low density polyethylene or linear low density polyethylene, metallocene polyethylene, biaxially-oriented polyethylene terephthalate (BoPET), ethylene-vinyl acetate/polyethylene (EVA/PE) and mixtures thereof.

Advantageously, the intermediate layer may extend continuously over the surface of the gas-impervious portion.

The outer and inner layers may preferably extend continuously on both sides of the intermediate layer so as to physically isolate the pigment from ambient atmosphere.

Preferably, the pigment may present a substantially constant concentration over the whole volume of the intermediate layer. The matrix containing the pigment may be a polymer, in particular an adhesive polymer, or a fluid medium, such as an ink or paint carrier.

For forming a polymer matrix, the polymer may be selected from the group consisting of polyethylene, in particular low density polyethylene or linear low density polyethylene, metallocene polyethylene, biaxially-oriented polyethylene terephthalate (BoPET), ethylene-vinyl acetate/polyethylene (EVA/PE) and mixtures thereof.

The porous portion may comprise a nonwoven fabric of high density polyethylene fibers.

Another embodiment relates to a process for manufacturing a multi-layer bag as described above. Said process comprises:
providing a porous sheet;
providing a gas-impervious sheet;
assembling the porous sheet to the gas-impervious sheet so as to form the bag.

Said process is characterized in that the gas-impervious sheet comprises an outer layer, an inner layer and an intermediate layer integrally formed together so that the intermediate layer is sealingly enclosed between the outer layer and the inner layer and in that the intermediate layer comprises a matrix and at least one pigment distributed within the matrix, the pigment being configured to change at least one optical property in reaction to an environment change resulting from a damage of the outer and/or inner layer.

If the matrix is a polymer, the step of providing the gas-impervious sheet may comprise simultaneously extruding the outer layer, the intermediate layer and the inner layer.

Alternatively, if the matrix is a fluid carrier, the step of providing the gas-impervious sheet may comprise applying the intermediate layer as an ink or paint onto the surface of at least one of the outer and inner layers.

Another embodiment relates to a process for packaging a medical device. Said process comprises the following steps:
providing a multi-layer bag as described above;
placing the medical device in the multi-layer bag;
closing the multi-layer bag;
sterilizing the medical device by exposing the multi-layer bag to a sterilizing gas, wherein the sterilizing gas is allowed to penetrate into the multi-layer bag through the porous portion.

According to an embodiment, the step of placing the medical device in the multi-layer bag comprises:
placing the medical device in a tub,
sealing the tub with a porous sheet configured to allow the multi-layer gas to penetrate into the bag, and
placing the tub in the multi-layer bag.

According to an embodiment, the medical device is a medical container and the step of placing the medical device in the tub comprises arranging a plurality of medical containers in a nest and placing the nest supporting the medical containers in the tub.

Another embodiment relates to a process for detecting a loss of integrity of a multi-layer medical packaging. Said process comprises:
packaging a medical device with the process as described above;
detecting a breach in the gas-impervious portion of the multi-layer bag by a change in the optical property of the pigment of the intermediate layer around the breach.

The step of detecting the breach may be carried out by:
visual inspection of the multi-layer bag, the optical property change of the pigment being a color change visible by a naked human eye; and/or
infrared or UV inspection, the optical property change of the pigment being visible under infrared or UV light,
infrared or UV inspection, the optical property change of the pigment being triggered by infrared or UV light generated by the inspection system.

BRIEF DESCRIPTION OF THE FIGURES

Other features, advantages and embodiments will appear in the detail description that follows, based on the appended drawings where.

Figure 1:
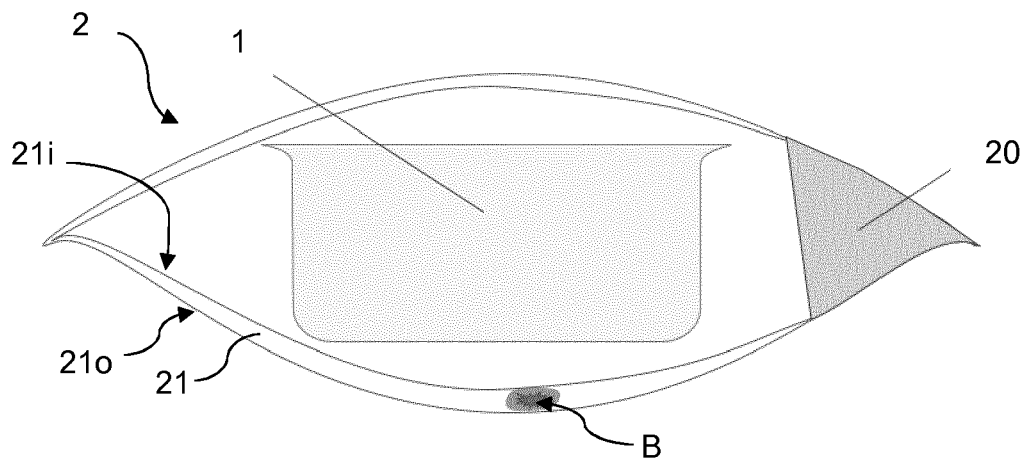
FIG. 1 is a schematic view of the packaging according to the invention.

For sake of legibility, the figures are not drawn to scale.

Reference numerals that are identical from one figure to another one designate the same element or at least elements fulfilling the same function.

DETAILED DESCRIPTION OF EMBODIMENTS OF THE INVENTION

FIG. 1 is a schematic view of a medical packaging according to the invention.

A medical device 1 is enclosed in a multi-layer bag 2.

The multi-layer bag comprises a porous portion 20 and a gas-impervious portion 21. The porous portion and gas-impervious portion are assembled side by side, thereby together defining a sealed enclosure for receiving one or more medical devices 1.

The porous portion 20 which is porous to gases, and particularly sterilization gases (e.g. ethylene oxide), is configured to allow said sterilizing gases to penetrate into the bag in order to decontaminate the medical device. The porous portion may be a made of a nonwoven fabric of high density polyethylene fibers, which is known in particular under the name TYVEK™. Said porous portion is however impermeable to contaminants including microorganisms, bacteria, etc.

The gas-impervious portion 21 is made of a stack of at least three layers that are integral with each other, i.e. the at least three layers form a single gas-impervious sheet and are not separable from each other.

The gas-impervious portion presents a permeability to gases which is much lower than the porous portion. Said permeability usually depends on the shelf life of the packaging, the gas(es) to which the portion has to be impervious, and may also depend on the thickness of the porous portion. The required permeability may be determined based on a maximum content of the considered gas(es) in the bag at the end of the shelf life of the packaging.

Figure 2:
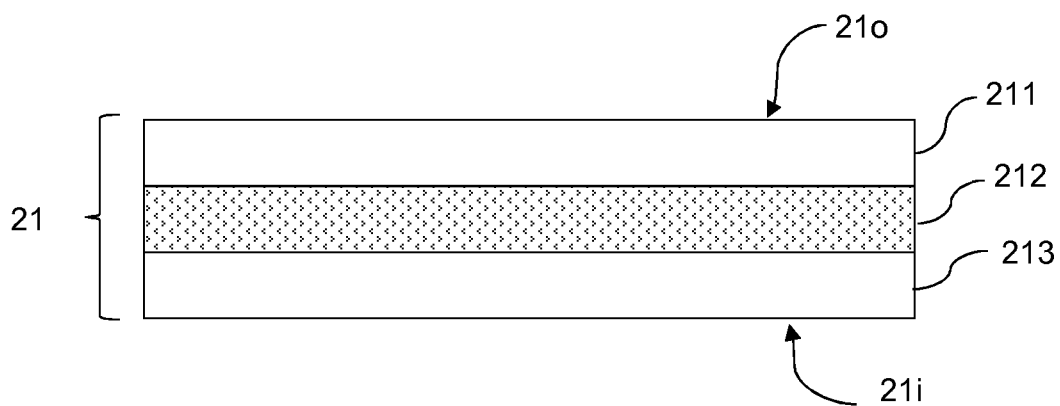
FIG. 2 is a sectional view of the gas-impervious portion of the multi-layer bag according to the invention.

As shown in FIG. 2, the gas-impervious portion 21 comprises an outer layer 211 that is located on the outer side 21o of the multi-layer bag, and an inner layer 213 that is located on the inner side 21i of the multi-layer bag.

Both the outer layer 211 and the inner layer 213 are impervious to gas and liquids. Contrary to portion 20, the layers 211 and 213 are substantially non-porous.

The thickness of the outer layer may be of the order of 1 to 100 µm, preferably between 5 and 70 µm, for example 12 µm, whereas the thickness of the inner layer may be of the order of 1 to 100, preferably between 5 and 70 µm, for example 51 µm.

The outer layer 211 and the inner layer 213 may typically comprise a polymer selected from the group consisting of polyethylene, in particular low density polyethylene (LDPE) or linear low density polyethylene (LLDPE), metallocene polyethylene, biaxially-oriented polyethylene terephthalate (BoPET), ethylene-vinyl acetate/polyethylene (EVA/PE) and mixtures thereof.

The outer layer 211 and the inner layer 213 may typically be produced by any conventional method, e.g. the outer layer 211 and the inner layer 213 may be extruded, blown, cast or laminated as described in US 2013/0095336.

The gas-impervious portion further comprises an intermediate layer 212 extending between the outer and inner layers 211, 213. The outer and inner layers extend continuously along both sides of the intermediate layer 212 so as to physically isolate said intermediate layer from ambient atmosphere. By "ambient atmosphere" is meant the present atmosphere that surrounds the multi-layer bag. This atmosphere is substantially the same inside and outside the bag due to the porous portion 20, except that, after sterilization of the bag, the atmosphere inside the bag is sterile whereas the atmosphere outside the bag is non-sterile.

The intermediate layer comprises a matrix in which a pigment is distributed.

The pigment is configured to change at least one optical property in reaction to an environment change caused by a breach or a perforation made in the gas-impervious portion, said change being detectable visually, by naked eye (using visible light) or using an infrared or ultraviolet light. The optical property may typically be a color of the pigment.

Said optical property is in a first condition when the multi-layer bag is being manufactured and then used to package the medical device. Once the gas-impervious portion has been formed, the first condition is supposed to remain the same as long as the integrity of the multi-layer bag is maintained since the inner and outer layers 211, 213 physically isolate the intermediate layer 212 (and thus the pigment) from ambient atmosphere.

If the optical property change of the pigment is not reversible, the atmosphere (hereinafter called first atmosphere) to which the pigment is exposed during manufacturing of the multi-layer bag may preferably be controlled in order to ensure that the optical property of the pigment remains in the first condition until the intermediate layer is sealingly enclosed between the outer and inner layers.

If the optical property change of the pigment is reversible, it may not be necessary to control the first atmosphere. Indeed, even if the pigment is exposed to an element of the atmosphere during the manufacture of the multi-layer bag that causes a change in its optical property, this optical property may change back to the first condition once the intermediate layer is embedded between the outer and inner layers since the pigment is then isolated from the above-mentioned element.

Figure 3:
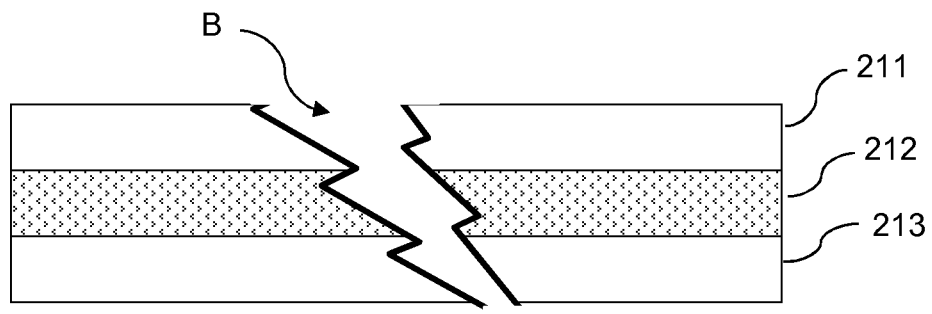
FIG. 3 is a sectional view of the gas-impervious portion of FIG. 2, with a breach in the multi-layer bag according to the invention.

The optical property of the pigment may change to a second condition only when the intermediate layer (and thus the pigment) is exposed to a different atmosphere (hereinafter called second atmosphere). Such an exposure may be generated by the creation of a breach B or a perforation in the gas-impervious portion, as shown in FIG. 3. Due to this breach or perforation, a portion of the intermediate layer 212 becomes exposed to the ambient atmosphere. The pigment present in this portion of the intermediate layer is thus caused to change its optical property to the second condition, thereby rendering the breach or perforation detectable.

A breach formed in only one of the inner and the outer layer may advantageously be detected thanks to the pigment. Indeed, even if the other layer, which is substantially non-porous, still protects the inside of the bag from contamination, the shelf life of the product contained in the bag may be reduced. Besides, if the breach is formed in the inner layer, the atmosphere inside the bag may be in contact with the intermediate layer, which may not be sterile and may thus contaminate the product contained inside the bag. Thus, detection of a partial breach may be of interest.

Preferably, the change of optical property of the pigment occurs only in the immediate vicinity of the breach or perforation. Thus, this change allows localizing the breach or perforation.

Preferably, the pigment is homogeneously present into the intermediate layer, meaning that a breach or a perforation may be detected on the whole surface of the gas-impervious portion of the multi-layer bag.

The concentration of the pigment within the matrix is selected so that the second condition is sufficiently different from the first condition to allow easy and safe detection of the location of the breach or perforation, depending on the detection means used.

Preferably, the concentration of the pigment is substantially constant over the whole volume of the intermediate layer.

Different types of pigments may be used. The skilled person is able to select the suitable pigment among pigments available on the market, depending on the situation to be detected.

According to an embodiment, the pigment changes color when in contact with water or moist. The pigment may also change color when in contact with $H_2O_2$ in a liquid state.

According to an embodiment, the pigment changes color when in contact with a determined gas such as $O_2$, $CO_2$, $N_2$, Ar, $H_2$, $H_2O_2$, NOX (nitrogen oxide), EtO or mixture thereof, preferably in contact with a determined concentration of said gases. For example, the pigment may comprise at least one of the following compounds: oxyhaemoglobin which can be oxidized by $O_2$, the oxidation generating a change of color, or palladium oxide which may be reduced into metal palladium by $H_2$, the reduction generating a change of color.

According to an embodiment, the pigment changes color in reaction to a pH change. For example, the pigment may comprise at least one of the following compounds: bromocresol purple, methyl red and bromothymol blue.

According to an embodiment, the pigment changes color when exposed to a change of radiation (light). This property may be applied when the inner and outer layers are opaque, the intermediate layer being exposed to visible, infrared or UV light when a breach is created in at least one of these layers. The light that triggers the optical property change may be the ambient light to which the multi-layer bag is exposed, in particular when the inspection is made by naked eye. Alternatively, the light that triggers the optical property change may be generated by an inspection system that emits a specific radiation such as ultraviolet or infrared. For example, the pigment may comprise an oxazine or bis-imidazole.

According to an embodiment, the pigment changes color when a mechanical pressure is exerted onto the intermediate layer.

Although the present description mentions "a pigment" for sake of conciseness, the matrix may contain two or more different pigments. These pigments may have different optical properties that may be caused by different environmental conditions (e.g. exposure to different gases) and/or by different levels of a given situation (e.g. different concentrations of a gas to which the pigments are exposed).

The matrix may also contain a pigment that does not react to an environmental change but that simply provides a base color of the intermediate layer. The combination of this non-reactive pigment with one or more pigment(s) configured to react to an environment change may allow obtaining the desired color for integrity and loss-of-integrity conditions.

In an embodiment, the matrix may contain a yellow non-reactive first pigment, a second pigment configured to transition from white to blue when exposed to oxygen and a third pigment configured to transition from white to blue or another color when exposed to humidity. In this way, as long as the integrity of the bag is maintained, the intermediate layer is yellow, but becomes green (combination of yellow and blue) when a breach is formed in the bag and the second pigment is exposed to oxygen.

In another embodiment, if it is desired that the intermediate layer is green as long as the integrity of the bag is maintained and red when a breach occurs in the outer and/or inner layer, it may be difficult to find a unique pigment providing such specific color transition. However, the skilled person may combine a first pigment which transitions from green to white when exposed to humidity and a second pigment which transitions from white to red when exposed to humidity. Both pigments may not react at the same level of humidity; for instance, the first pigment may react to a relatively lower level of humidity whereas the second pigment may react to a relatively higher level of humidity. As a result, different colors may be obtained after a breach is made in the inner and/or outer layer of the bag:

- if the bag is exposed to a low level of humidity, the first pigment is green and the second pigment is white; the resulting color is green;
- if the bag is exposed to a high level of humidity, the first pigment becomes white and the second pigment becomes red; the resulting color is red;
- if the bag is exposed to a medium level of humidity, intermediate between low and high levels, the first pigment starts transitioning from green to white and the second pigment begins transitioning from white to red; the resulting color may be white;
- a brown color (combination of green and red) may be observed when the bag is exposed to a medium level of humidity if the first pigment has not reacted, remaining green while the second pigment reacts becoming red, e.g. due to a problem during the manufacturing of the gas-impervious portion causing inactivation of the first pigment; in this way, the combination of at least two pigments also allows detecting malfunctions of the pigment(s).

In some embodiments, a pigment may be selected so as to change its optical property when the bag has attained a prescribed shelf life. In this case, account is taken of the low permeability of the inner and outer layers to determine a quantity of gas(es) passing through these layers over time which is sufficient to trigger a change in an optical property of the pigment.

In some embodiments, the pigment is contained in a polymer matrix. In some embodiments, the polymer may be an adhesive and may thus allow bonding the inner and outer layers of the gas-impervious portion.

The polymer matrix may be selected from the group consisting of polyethylene, in particular low density polyethylene (LDPE) or linear low density polyethylene (LLDPE), metallocene polyethylene, biaxially-oriented polyethylene terephthalate (BoPET), ethylene-vinyl acetate/polyethylene (EVA/PE) and mixtures thereof.

In some embodiments, the pigment is contained in an ink or a paint. The matrix may thus be a fluid carrier (liquid or paste) which may include a solvent and additives such as solubilizers, surfactants, etc.

If necessary, at least one additional layer (not shown) may be provided between the outer layer and the intermediate layer, and/or between the intermediate layer and the inner layer, for example to increase adhesion between these layers, or to impart additional functional properties to the gas-impervious portion. Said additional layer may comprise a polymer selected from the group consisting of anhydride modified linear low density polyethylene, low density polyethylene, linear low density polyethylene, or mixture thereof. The thickness of said additional layer may be comprised between 0.5 and 50 μm, typically 2 μm.

Preferably, the gas-impervious portion has a greater surface than the porous portion. The surface of the porous portion is generally defined to be sufficient to allow an efficient decontamination of the medical device, while being limited in order to reduce the porosity of the bag after sterilization. Preferably, the surface ratio of the gas-impervious portion with respect to the porous portion is greater than 0.8, preferably greater than 0.9, preferably greater than 0.95.

Besides, the intermediate layer advantageously extends over more than 90% of the surface of the gas-impervious portion, preferably it extends over the whole surface of the gas-impervious portion, in order to maximize the chance of detecting a damage caused to the multi-layer bag.

On FIG. 1, the medical device 1 is represented in the form of a tub (e.g. intended to receive medical containers such as syringes), but it could of course be any other type of medical device that needs to be kept sterile.

If the pigment is contained in a polymer matrix, the gas-impervious portion may be made by coextrusion of the layers 211, 212, 213, in a controlled atmosphere as explained above.

To that end, the polymers that constitute each layer may be fused in an extruder and laminated together to form an integral sheet made of the at least three layers.

The pigment may be added as a masterbatch to the polymer forming the matrix of the intermediate layer before the fusion step. It may be intimately mixed with the fused polymer in the extruder, in order to be distributed substantially homogeneously throughout the intermediate layer.

If the pigment is contained in an ink or paint, the ink or paint may be applied over the surface of at least one of the outer and inner layers of the gas-impervious portion, before assembly of said layers. The application of the ink or paint and assembly of the layers may be done in a controlled atmosphere as explained above.

The gas-impervious sheet may be then cut to the suitable dimension and assembled to the porous portion to make the multi-layer bag. The gas-impervious portion may be heat-sealed to the bag.

The multi-layer bag may be used as follows, for example for packaging medical containers such as syringes.

In a manner known per se, a plurality of medical containers is arranged in a nest, the nest is placed in a tub and the tub is sealed with a porous sheet, e.g. made of TYVEK™.

The sealed tub is then placed in a multi-layer bag as described above. Possibly, the multi-layer bag is placed in another multi-layer bag to increase the protection of the medical containers against contamination.

Then, the medical containers are sterilized by providing an atmosphere comprising a sterilizing gas, the sterilizing gas being allowed to enter into the bag through the porous portion.

Depending on the type of pigment, the detection and localization of a breach in a multi-layer bag may be carried out by an operator under visible light (using his naked eye) or with an inspection system using ultraviolet (UV) or infrared (IR) light to reveal a change of optical property of the pigment.

Figure 4:
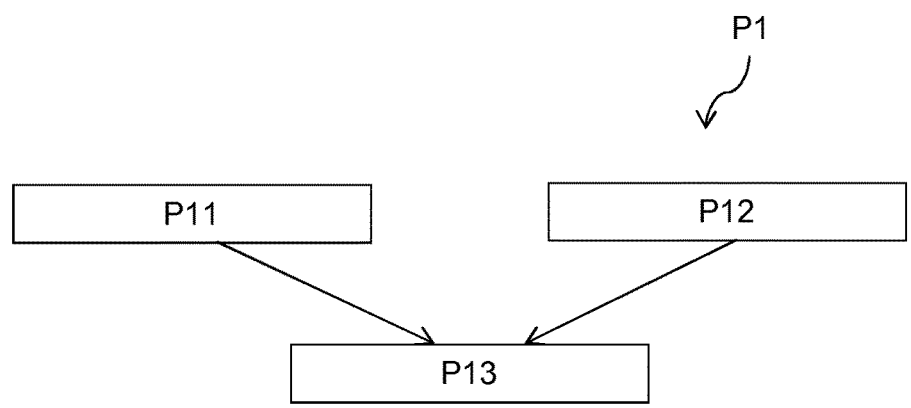
FIG. 4 is a schematic view of a process for manufacturing a multi-layer bag according to the invention.

As schematically illustrated on FIG. 4, the invention also relates to a process P1 for manufacturing a multi-layer bag as previously described, said process comprising the following steps:

P11: providing a porous sheet;
P21: providing a gas-impervious sheet;
P13: assembling the porous sheet to the gas-impervious sheet so as to form the bag;
wherein the gas-impervious sheet comprises an outer layer, an inner layer and an intermediate layer integrally formed together so that the intermediate layer is sealingly enclosed between the outer layer and the inner layer and the intermediate layer comprises a matrix and a pigment distributed within the matrix.

Preferably, in the process P1, the step of providing the gas-impervious sheet comprises simultaneously extruding the outer layer, the intermediate layer and the inner layer. Advantageously, in P1, the porous sheet and the gas-impervious sheet respectively correspond to the porous portion and the gas-impervious portion described above. Typically, the characteristics of the outer layer, the inner layer and the intermediate layer mentioned for the multi-layer bag of the invention applied for P1.

Figure 5:
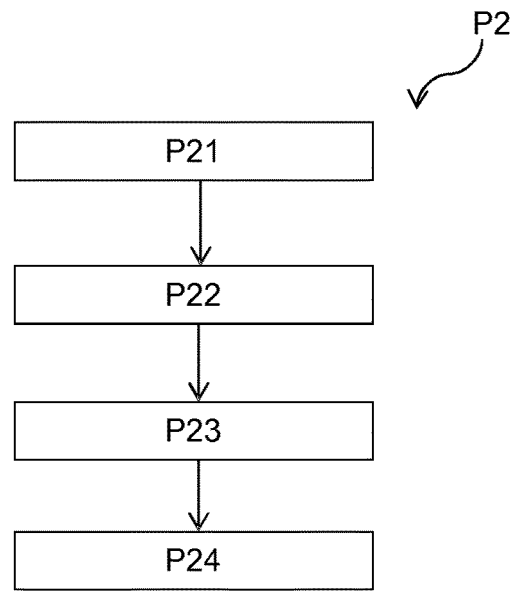
FIG. 5 is a schematic view of a process for packaging a medical device using a multi-layer bag according to the invention.

As schematically illustrated on FIG. 5, the invention also relates to a process P2 for packaging a medical device, comprising the following steps:

P21: providing a multi-layer bag as previously described; the multi-layer bag is advantageously produced by the process P1;
P22: placing the medical device in the multi-layer bag;
P23: closing the multi-layer bag;
P24: sterilizing the medical device by exposing the multi-layer bag to a sterilizing gas, such as ethylene dioxide, wherein the sterilizing gas is allowed to penetrate into the multi-layer bag through the porous portion.

Figure 6:
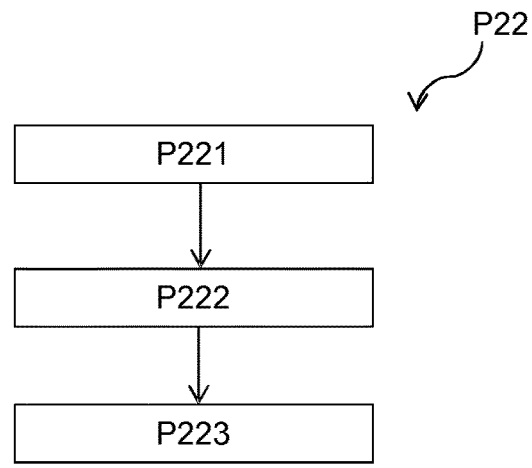
FIG. 6 is a schematic view of the step of placing the medical device in the multi-layer bag in the process of FIG. 5.

Preferably, in the process P2, the step P22 of placing the medical device in the multi-layer bag comprises (see FIG. 6):

P221: placing the medical device in a tub,
P222: sealing the tub with a porous sheet configured to allow the multi-layer gas to penetrate into the bag, and
P223: placing the tub in the multi-layer bag.

Advantageously, the multi-layer bag is closed by heat-sealing with any methods known from the skilled person.

Advantageously, in the process P2, the medical device is a medical container and the step of placing the medical device in the tub comprises arranging a plurality of medical containers in a nest and placing the nest supporting the medical containers in the tub.

Figure 7:
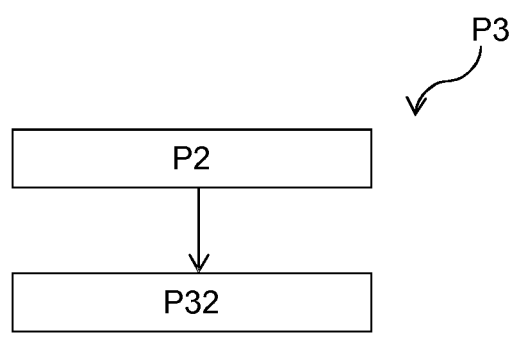
FIG. 7 is a schematic view of a process for detecting a loss of integrity of a medical packaging comprising a multi-layer bag according to the invention.

As schematically illustrated in FIG. 7, the invention also relates to a process P3 for detecting a loss of integrity of a medical packaging, characterized in that it comprises:

packaging a medical device with the process P2;
detecting (step P32) a breach in the gas-impervious portion of the multi-layer bag by a change in the optical property of the pigment of the intermediate layer around the breach.

Preferably, in the process P3, the step of detecting the breach is carried out by visual inspection of the multi-layer bag, the optical property change of the pigment being a color change visible by a naked human eye; and/or
infrared or UV inspection, the optical property change of the pigment being visible under infrared or UV light,
infrared or UV inspection, the optical property change of the pigment being triggered by infrared or UV light generated by the inspection system.

The detection principle may also be advantageous in other applications where the multi-layer bag does not include any porous portion. The multi-layer bag forms a gas-impervious enclosure, wherein at least one portion of said enclosure comprises an outer layer, an inner layer and an intermediate layer integrally formed together so that the intermediate layer is sealingly enclosed between the outer layer and the inner layer, and the intermediate layer comprises a matrix and a pigment distributed within the matrix, the pigment being configured to change at least one optical property in reaction to an environment change resulting from a damage of the outer and/or inner layer. Preferably, the whole enclosure is formed of said assembly of the outer layer, intermediate layer and inner layer so that a breach may be detected in any place of the enclosure.

The invention claimed is:

1. A multi-layer bag comprising a porous portion configured to allow a sterilizing gas to penetrate into the multi-layer bag and a gas-impervious portion, wherein the gas-impervious portion comprises an outer layer, an inner layer and an intermediate layer integrally formed together so that the intermediate layer is sealingly enclosed between the outer layer and the inner layer so as to be physically isolated from inner and outer environment of the multi-layer bag, and wherein the intermediate layer comprises a matrix and at least one pigment distributed within the matrix, the at least one pigment being configured to change at least one optical property in reaction to an environment change resulting from a damage of the outer and/or inner layer.

2. The multi-layer bag of claim 1, wherein the at least one pigment is configured to change color in at least one situation selected from the group comprising:
(i) the intermediate layer is in contact with water or moist;
(ii) the intermediate layer is in contact with a gas selected from the group comprising $O_2$, $CO_2$, $N_2$, Ar, $H_2$, $H_2O_2$, EtO, or mixture thereof;
(iii) the intermediate layer is exposed to a pH change;
(iv) the intermediate layer is exposed to a change of radiation; or
(v) a mechanical pressure is exerted onto the intermediate layer.

3. The multi-layer bag of claim 1, wherein the intermediate layer comprises at least two different pigments distributed within the matrix.

4. The multi-layer bag of claim 3, wherein at least two of the at least two different pigments have different optical properties in reaction to an environment change resulting from a damage of the outer and/or inner layer.

5. The multi-layer bag of claim 4, wherein at least two of the at least two different pigments are configured to change color in a different situation, the different situations comprising:
(i) the intermediate layer is in contact with water or moist;
(ii) the intermediate layer is in contact with a gas selected from the group comprising $O_2$, $CO_2$, $N_2$, Ar, $H_2$, $H_2O_2$, EtO, or mixture thereof;
(iii) the intermediate layer is exposed to a pH change;
(iv) the intermediate layer is exposed to a change of radiation; or
(v) a mechanical pressure is exerted onto the intermediate layer.

6. The multi-layer bag of claim 4, wherein at least two of the at least two different pigments are configured to change color in reaction to different levels of a situation, the same situation comprising:
(i) the intermediate layer is in contact with water or moist;
(ii) the intermediate layer is in contact with a gas selected from the group comprising $O_2$, $CO_2$, $N_2$, Ar, $H_2$, $H_2O_2$, EtO, or mixture thereof;
(iii) the intermediate layer is exposed to a pH change;
(iv) the intermediate layer is exposed to a change of radiation; or
(v) a mechanical pressure is exerted onto the intermediate layer.

7. The multi-layer bag of claim 1, wherein at least one of the outer layer and the inner layer comprises a polymer selected from the group consisting of: polyethylene, low density polyethylene or linear low density polyethylene, metallocene polyethylene, biaxially-oriented polyethylene terephthalate (BoPET), ethylene-vinyl acetate/polyethylene (EVA/PE), and mixtures thereof.

8. The multi-layer bag of claim 1, wherein the matrix comprises a polymer selected from the group consisting of polyethylene, low density polyethylene or linear low density polyethylene, metallocene polyethylene, biaxially-oriented polyethylene terephthalate (BoPET), ethylene-vinyl acetate/polyethylene (EVA/PE), and mixtures thereof.

9. The multi-layer bag of claim 1, wherein the matrix comprises a fluid carrier.

10. The multi-layer bag of claim 1, wherein the outer and inner layers extend continuously on both sides of the intermediate layer so as to physically isolate the at least one pigment from ambient atmosphere.

11. The multi-layer bag of claim 1, wherein the at least one pigment presents a substantially constant concentration over the whole volume of the intermediate layer.

12. The multi-layer bag of claim 1, wherein the porous portion comprises a nonwoven fabric of high density polyethylene fibers.

13. A process for packaging a medical device comprising:
providing a multi-layer bag as claimed in claim 1;
placing the medical device in the multi-layer bag;
closing the multi-layer bag; and
sterilizing the medical device by exposing the multi-layer bag to a sterilizing gas, wherein the sterilizing gas is allowed to penetrate into the multi-layer bag through the porous portion.

14. The process of claim 13, wherein the step of placing the medical device in the multi-layer bag comprises:
placing the medical device in a tub;
sealing the tub with a porous sheet configured to allow a multi layer gas to penetrate into the multi-layer bag; and
placing the tub in the multi-layer bag.

15. The process of claim 14, wherein the medical device is a medical container and the step of placing the medical device in the tub comprises arranging a plurality of medical containers in a nest and placing the nest supporting the medical containers in the tub.

16. A process for detecting a loss of integrity of a medical packaging comprising:
packaging a medical device with the process as claimed in claim 13;
detecting a breach in the gas-impervious portion of the multi-layer bag by a change in at least one optical property of the at least one pigment of the intermediate layer around the breach.

17. The process of claim 16, wherein the step of detecting the breach is carried out by at least one method selected from the group comprising:
visual inspection of the multi-layer bag, the at least one optical property change of the at least one pigment being a color change visible by a naked human eye;
infrared or UV inspection, the at least one optical property change of the at least one pigment being visible under infrared or UV light; or
infrared or UV inspection, the at least one optical property change of the at least one pigment being triggered by infrared or UV light generated by an inspection system.

18. A process for manufacturing a multi-layer bag comprising:
providing a porous sheet;
providing a gas-impervious sheet; and
assembling the porous sheet to the gas-impervious sheet so as to form the bag,
wherein the gas-impervious sheet comprises an outer layer, an inner layer and an intermediate layer integrally formed together so that the intermediate layer is sealingly enclosed between the outer layer and the inner layer so as to be physically isolated from inner and outer environment of the multi-layer bag, and wherein the intermediate layer comprises a matrix and at least one pigment distributed within the matrix, the at least one pigment being configured to change at least one optical property in reaction to an environment change resulting from a damage of the outer and/or inner layer.

19. The process of claim 18, wherein the matrix is a polymer matrix and the step of providing the gas-impervious sheet comprises simultaneously extruding the outer layer, the intermediate layer, and the inner layer.

20. The process of claim 18, wherein the matrix is a fluid carrier and the step of providing the gas-impervious sheet comprises applying the intermediate layer as an ink or paint onto a surface of at least one of the outer and inner layers.

* * * * *

UNITED STATES PATENT AND TRADEMARK OFFICE
CERTIFICATE OF CORRECTION

PATENT NO. : 12,246,107 B2
APPLICATION NO. : 17/289978
DATED : March 11, 2025
INVENTOR(S) : Maxime Nicolas et al.

Page 1 of 1

It is certified that error appears in the above-identified patent and that said Letters Patent is hereby corrected as shown below:

In the Claims

Column 12, Line 28, Claim 14, delete "multi layer gas" and insert -- gas --

Signed and Sealed this
Twenty-ninth Day of April, 2025

Coke Morgan Stewart
*Acting Director of the United States Patent and Trademark Office*